United States Patent [19]

Lamaziere

[11] 4,256,153

[45] Mar. 17, 1981

[54] DEVICE FOR SIMULTANEOUS TRANSFER OF A PLURALITY OF LIQUIDS

[75] Inventor: Jacques Lamaziere, Paris, France

[73] Assignee: Societe Francaise pour le Developpement de l'Automatisme en Biologie, Paris, France

[21] Appl. No.: 56,009

[22] Filed: Jul. 9, 1979

[51] Int. Cl.³ .............................................. B65B 3/04
[52] U.S. Cl. ................................... 141/84; 141/238; 141/262; 141/270; 211/71
[58] Field of Search .......................... 141/84, 234–248, 141/250–284, 1, 4, 5, 2, 18, 25, 26, 27, 367–381, 98, 129–191; 211/2, 71, 74

[56] References Cited

U.S. PATENT DOCUMENTS 3,833,031  9/1974  Fechheimer ........................... 141/84

Primary Examiner—Houston S. Bell, Jr.

Attorney, Agent, or Firm—Merriam, Marshall & Bicknell

[57] ABSTRACT

The invention relates to a device for simultaneously transferring, in both directions, a plurality of quantities of liquids between a first receptacled assembly disposed in a first arrangement and a second receptacled assembly disposed in a second arrangement of different disposition and/or dimensions, said device comprising a plurality of vertical syringes of which the needles are arranged in register with said first receptacled assembly and a connecting assembly comprising on the one hand a plurality of orifices arranged in register with the needles of said syringes and on the other hand a plurality of conduits arranged in register with the receptacles of said second assembly, each of said orifices being connected to one of said conduits. The invention finds particular application in the handling of microdoses of liquids, particularly for biological, serological . . . microtests.

4 Claims, 5 Drawing Figures

DEVICE FOR SIMULTANEOUS TRANSFER OF A PLURALITY OF LIQUIDS

The present invention relates to a device for simultaneously transferring a plurality of doses of liquids.

Techniques are already known which enable microtests to be effected, particularly on erythrocytes, leucocytes or on other cellular or microbial elements, by examining a plurality of microdoses of liquids by means of a plurality of reagents. Such techniques have numerous applications in the examination of serological and biochemical liquids and suspensions, particularly in the field of cytology and immuno-haematology and they use, both for transporting the liquids and for carrying out the reactions, micro-receptacled assemblies, for example constituted by plates provided with a plurality of cavities, each of which forms one of said receptacles.

Of course, because of the small doses of liquids handled (from a fraction of a microliter to a few milliliters), these techniques require equipment especially provided for such a small scale.

It is particular object of the present invention to provide a device allowing an easy transition between the equipment currently used in laboratories, of normal scale, and the equipment especially intended for handling microdoses of liquids.

The device of the invention makes it possible to transfer, simultaneously and in either direction, a plurality of quantities of liquids between a first receiver having receptacles disposed in a first arrangement, and a second receiver having receptacles disposed in a second arrangement of different disposition and/or dimensions. To this end, the device comprises a first receiver having a plurality of receptacles, a plurality of vertical syringes, having needles which are arranged in register with the receptacles of said first receiver, a second receiver including a receptacled assembly having a plurality of receptacles, a connecting assembly comprising a plurality of orifices arranged to register with the needles of said syringes and a plurality of conduits, each of said conduits having one end connected to one of said orifices, the other ends of said conduits being arranged to register with the receptacles of said receptacled assembly, means for bringing the receptacles of said receptacled assembly into register with said conduits of said connecting assembly and means including a carriage for bringing a selected one of said first and second receivers into register with the needles of said syringes, whereby said needles register respectively with the receptacles of said first receiver or with the orifices of said second receiver.

In the device of the invention, the bodies of said syringes are advantageously fixed and the plunger rods thereof slide fast with a slide member moved by first drive means axially with respect to said rods. There is also provided, beneath the needles of said syringes, a vertically movable carriage adapted to receive a selected one of said first or second receivers. Second drive means are provided to move the carriage to a position wherein the needles of said syringes can cooperate either with the receptacles of the first receiver or with the receptacles of the second receiver via said connecting assembly.

The conduits of the connecting assembly may be needles, each orifice being connected to the corresponding needle, for example by a flexible tube.

The above-mentioned valves may also be intended to prevent the tubes from emptying by flow, when the needles are withdrawn from the orifices, for example to cause them to cooperate again with the first receiver.

The first receiver and the second receptacled assembly combined with the connecting assembly are advantageously provided in the form of two interchangeable units receivable in said carriage.

In the second receiver, the receptacled assembly is preferably mounted so as to be removable.

The invention will be more readily understood on reading the following description with reference to the accompanying drawings, in which.

Figure 1:
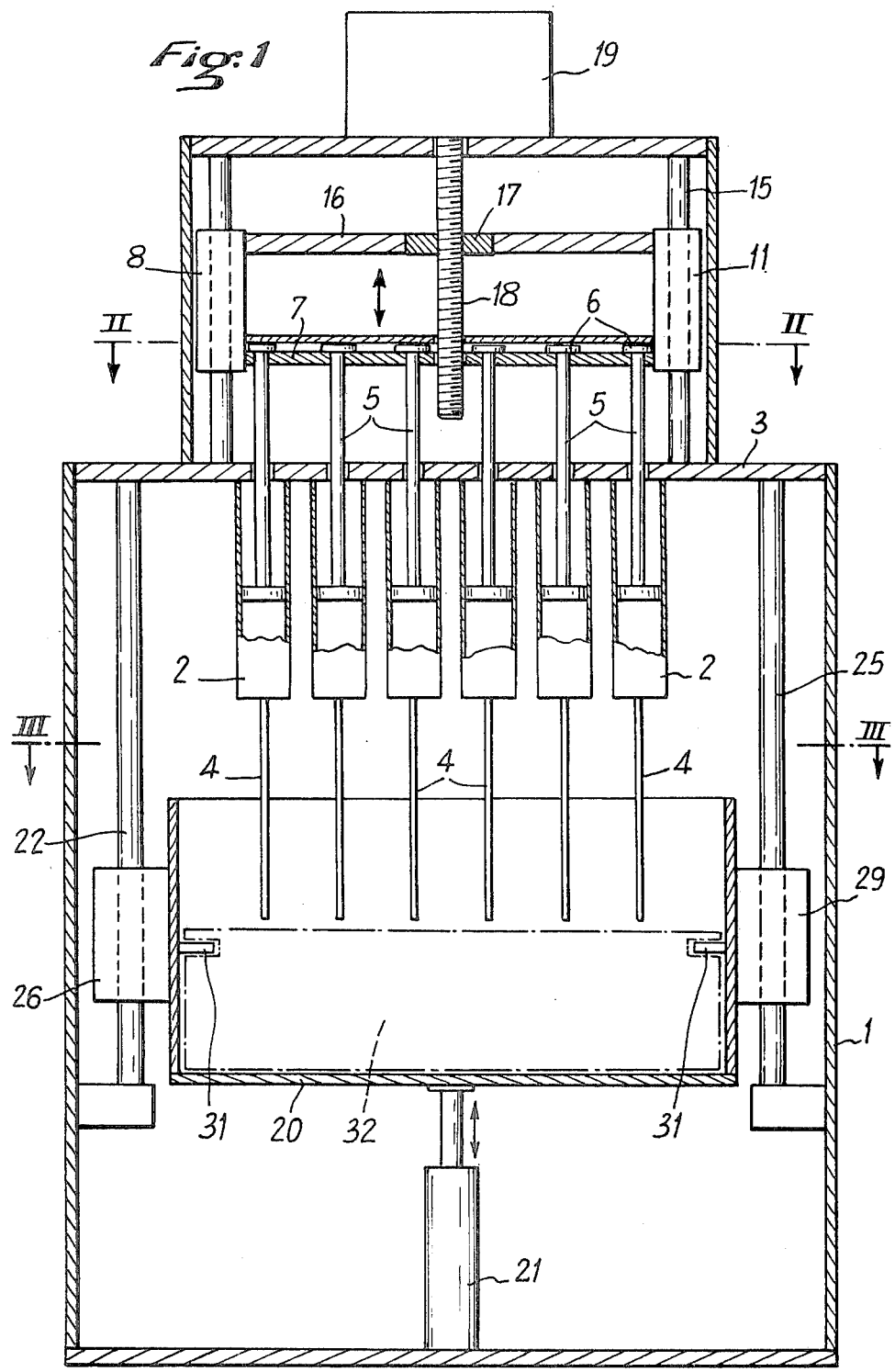
FIG. 1 is a view in vertical section of an embodiment of a device according to the invention.
Figure 2:
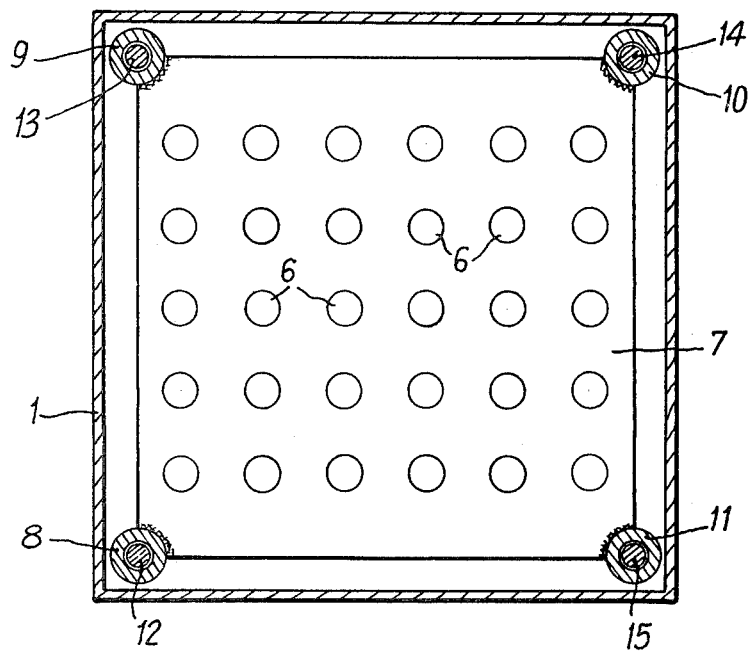
FIG. 2 is a horizontal section, along line II—II of FIG. 1.
Figure 3:
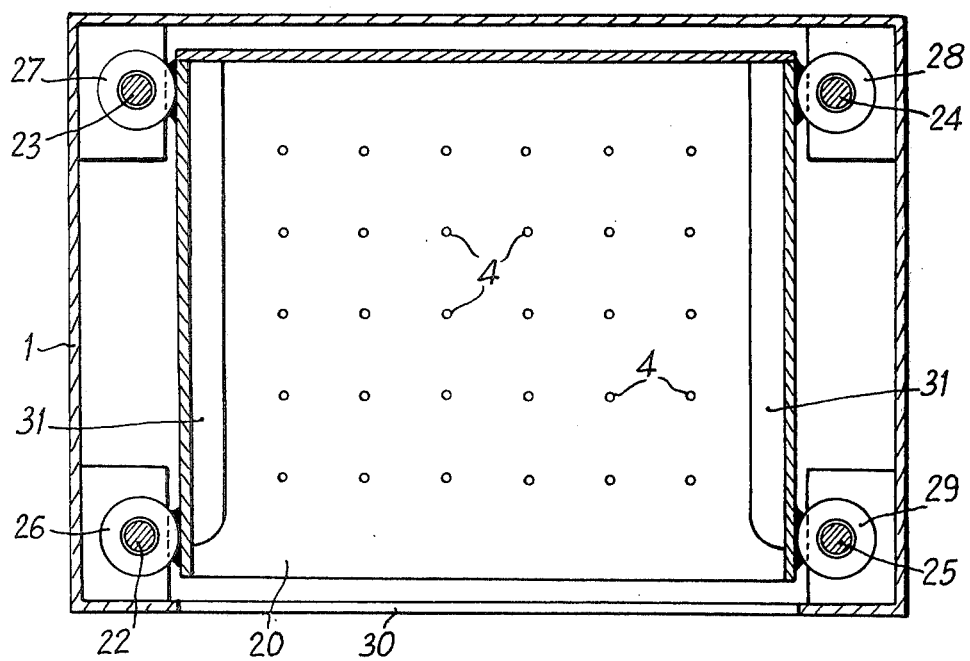
FIG. 3 is a horizontal section, along line III—III of FIG. 1.

Referring now to the drawings, FIG. 1 shows the device according to the invention which comprises a frame 1, inside which are arranged a plurality of syringes 2, distributed in lines and columns. In the example shown in the Figures, the device comprises thirty syringes 2 distributed in five rows of six syringes. The bodies thereof are made fast with a horizontal wall 3 of the frame 1, so that their needles 4 are directed downwardly. The plunger rods 5 of the syringes 2 freely pass through the wall 3 and are fast, at their upper end 6, with a movable horizontal plate 7. To this end the horizontal plate 7 is fast at its periphery with four ball-bearing sleeves 8 to 11, each mounted on a vertical rod 12 to 15 respectively. The sleeves 8 to 11 are further fast with another horizontal plate 16, of which the central part comprises a nut 17, with which a vertical threaded rod 18 cooperates, said latter being capable of being rotated about its axis by first drive means comprising an electric motor 19.

Furthermore, beneath the needles 4 of the syringes 2 there is disposed a carriage 20 that may move vertically for example under the action of a pneumatic jack 21. The carriage 20 is slidably guided by four vertical rods 22 to 25 fast with the frame 1 and on which are respectively mounted ball-bearing sleeves 26 to 29 fast with the periphery of the carriage 20. Said latter is open at the front, opposite an opening 30 in the frame 1, and comprises a system of guides 31.

A removable receiver 32 may be mounted in the carriage 20 with the aid of the system of guides 31 and through the opening 30.

Figure 4:
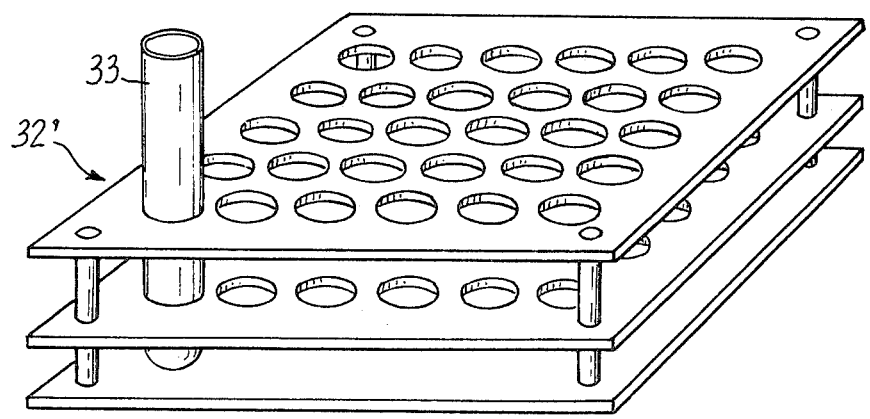
FIG. 4 is a view in perspective of a tube support for the device of FIG. 1.

FIG. 4 shows a first example 32' for the receiver 32. The receiver 32' is a tray for carrying a plurality of vertical tubes 33, disposed in the same manner as the syringes 2.

Figure 5:
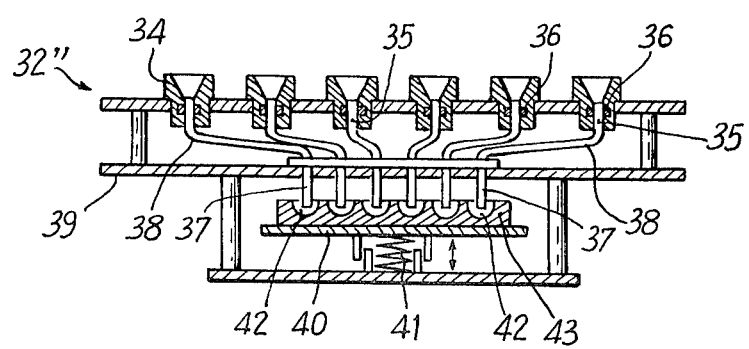
FIG. 5 is a schematic view in section of a connecting assembly for the device of FIG. 1.

FIG. 5 shows a second example 32" for the receiver 32. The receiver 32" comprises, a plurality of end pieces 34, distributed in the same arrangement as the syringes 2 and provided with conduits 35, with O-rings 36 and optional nonreturn valves, for the introduction of the needles 4 of said syringes and a plurality of needles 37, each of which is connected to a conduit 35 by a flexible tube 38, of the catheter type. The end pieces 34 and the needles 37 are fast with a common frame 39 with respect to which a plate 40 sliding vertically and supported by a spring 41, is also mounted.

The dimensions and/or arrangement of the needles 37 are different from those of needles 4 but correspond to those of cavities 42 of a microtest plate 43, removably supported by the plate 40.

The device according to the invention may function as follows:

The plungers of the syringes and the carriage 20 being in their maximum low position, first receiver 32' is introduced into the carriage 20 through the opening 30, the tubes 33 containing different or identical liquids. The pneumatic jack 21 is then actuated to raise the carriage 20 and cause each of the needles 4 to penetrate in a tube 33. Then the electric motor 19 is switched on to draw the rods 5 upwardly, this resulting in each syringe 2 being filled with the liquid contained in the corresponding tube 33. When the syringes 2 are sufficiently filled, the electric motor 19 is stopped and the jack 21 is again actuated so that it lowers the carriage 20. When said latter is in low position, first receiver 32' is withdrawn and it is replaced by second receiver 32", after which the jack 21 is again actuated upwardly, until each of the needles 4 penetrates in an end piece 34. The motor 19 is than actuated so that each syringe 2 delivers in the corresponding cavity 42 of the plate 43 the desired quantity of liquid. When this is obtained, the plate 43 is removed (by lowering the tray 40 against the action of spring 41), and it is replaced by an empty one, and so on, as long as there is liquid in the syringes 2. When said latter are empty, they may be filled again, by means of first receiver 32', in the manner described hereinabove.

Thus, due to the invention, a device is obtained which allows an easy transition between microdoses and currently handled doses of liquid.

It will noted that the syringes 2 may possibly serve as reaction tubes: for example, reagents contained in the cavities 42 may be drawn up in order to react with the liquids in said syringes. Or they may draw up reagents contained in the cavities 42 to deliver them in the tubes 33 of the assembly 32'.

I claim:

1. A device for simultaneously transferring a plurality of quantities of liquid in either direction between two receivers having receptacles for said liquids disposed in different arrangements, said device comprising:
    a plurality of vertical syringes having bodies, plunger rods, and needles,
    means for actuating all said syringes simultaneously so that each of them draws up or delivers a quantity of liquid through its associated needle,
    a first receiver having a plurality of first receptacles arranged to register with the needles of said syringes,
    a second receiver comprising a connecting assembly having a plurality of orifices arranged to register with the needles of said syringes, a receptacled assembly having a plurality of second receptacles in an arrangement differing from that of said first receptacles, and a plurality of conduits for liquid flow, each conduit having one end connected to one of said orifices, the other end of each conduit being arranged to register with one of said second receptacles, and means for bringing said second receptacles into register with said conduits,
    vertically movable carriage means disposed below said needles and adapted to hold interchangeably a selected one of said first and second receivers, and
    first drive means for moving said selected one of said receivers held by said carriage into register with said needles, whereby said needles register respectively with said first receptacles or with said orifices.

2. The device of claim 1, wherein the orifices of said connecting assembly are provided with sealing means in order to be hermetically fitted on said needles.

3. The device of claim 1 wherein the bodies of said syringes are fixed relative to each other,
    said actuating means comprising a slide member to which are affixed the plunger rods of said syringes, and
    second drive means for moving said slide member axially with respect to said rods whereby each syringe is adapted to simultaneously draw up or deliver a quantity of liquid.

4. The device of claim 1 wherein each of said conduits includes a needle adapted to register with one of said second receptacles.

* * * * *

UNITED STATES PATENT AND TRADEMARK OFFICE
CERTIFICATE OF CORRECTION

PATENT NO. : 4,256,153
DATED : March 17, 1981
INVENTOR(S) : JACQUES LAMAZIERE

It is certified that error appears in the above–identified patent and that said Letters Patent are hereby corrected as shown below:

Col. 1, after line 65, insert the following paragraph:

--The orifices of said connecting assembly are preferably provided with sealing means in order to be hermetically fitted on said needles. Said orifices may further comprise a valve allowing liquids to flow only if the needles are driven into said orifices beyond a certain position.--

Signed and Sealed this

Ninth Day of June 1981

[SEAL]

Attest:

RENE D. TEGTMEYER

Attesting Officer    Acting Commissioner of Patents and Trademarks